United States Patent [19]

Searle et al.

[11] 3,993,774
[45] Nov. 23, 1976

[54] PESTICIDAL CYCLOPROPANE DERIVATIVES

[75] Inventors: Robert J. G. Searle, Rodmersham Green, near Sittingbourne; Roger E. Woodall, Borden, near Sittingbourne, both of England

[73] Assignee: Shell Oil Company, Houston, Tex.

[22] Filed: Sept. 9, 1975

[21] Appl. No.: 611,760

Related U.S. Application Data

[62] Division of Ser. No. 442,994, Feb. 15, 1974, Pat. No. 3,927,068.

[30] Foreign Application Priority Data

Feb. 16, 1973 United Kingdom............. 7685/73

[52] U.S. Cl.............................. 424/305; 424/304
[51] Int. Cl.².......................................... A01N 9/24
[58] Field of Search............................ 424/305, 306

[56] References Cited
UNITED STATES PATENTS 3,835,176  9/1974  Matsuo et al.................. 260/465 D
3,862,174  1/1975  Mizutani et al................ 260/240 R

OTHER PUBLICATIONS

Chemical Abstracts, vol. 79 (1973), p. 143527v.

*Primary Examiner*—V. D. Turner

[57] ABSTRACT

Cyclopropane derivatives of the formula

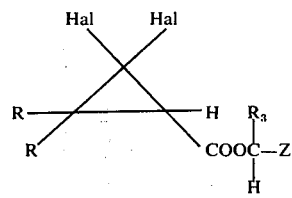

wherein each R is alkyl, $R_3$ is optionally substituted hydrocarbyl, each Hal represents halogen, and Z represents an optionally substituted phenyl group are useful as pesticides.

10 Claims, No Drawings

PESTICIDAL CYCLOPROPANE DERIVATIVES

CROSS-REFERENCE TO RELATED APPLICATIONS

This application is a division of Ser. No. 442,994, filed Feb. 15, 1974 now U.S. Pat. No. 3,927,068, issued Dec. 16, 1975.

DESCRIPTION OF THE PRIOR ART

It is well known that various esters of chrysanthemum carboxylic acid, or 2,2-dimethyl-3-(2-methylpropenyl)cyclopropanecarboxylic acid, are useful as insecticides. They suffer from the disadvantages of high cost and short persistence which are generally related to the chemical structure — in particular, the isobutenyl side chain of the acid. This side chain causes synthesis problems and represents a site for oxidative, thermal, and photochemical degradation.

Applicants have now succeeded in preparing new types of esters based on a cyclopropane nucleus which esters are low in cost and have excellent insecticidal activity as compared with the prior art esters of chrysanthemum carboxylic acid.

SUMMARY OF THE INVENTION

This invention relates to novel cyclopropane derivatives which exhibit pesticidal, especially insecticidal and acaricidal, properties.

Accordingly, the present invention provides cyclopropane derivatives of general formula:

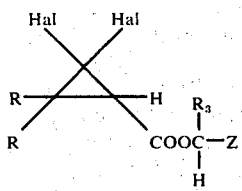

wherein each R represents an alkyl group, each Hal represents a halogen atom; $R_3$ represents an optionally substituted alkyl, cycloalkyl, alkenyl, alkynyl or aryl group; and Z represents an optionally substituted phenyl group. Examples of suitable substituents on the optionally substituted groups are, for $R_3$ a cyano group, and for Z an alkyl, alkenyl, aralkyl, aryloxy or alkynyloxy group.

PREFERRED EMBODIMENT OF THE INVENTION

Preferred cyclopropane derivatives are those of formula I wherein R represents an alkyl group of 1–6 carbon atoms especially methyl; each Hal represents a chlorine atom, $R_3$ represents an alkyl, cylcoalkyl, cyanoalkyl, or alkenyl group of up to 6 carbon atoms, for example methyl, cyclohexyl, cyanomethyl, vinyl or propenyl, an alkynyl group of up to 8 carbon atoms, for example phenylethynyl or ethynyl, or a phenyl group; and Z represents a phenyl group optionally substituted by one or more alkyl, alkenyl, aralkyl, aryloxy or alkynyloxy groups of up to 8 carbon atoms, for example, methyl, allyl, benzyl, phenoxy or propynyloxy.

The cyclopropane derivatives of the invention may be prepared by a process which comprises reacting a compound of formula:

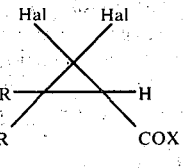

with a compound of formula:

wherein one of the groups X and Y represents a halogen, suitably chlorine, atom and the other represents a hydroxy group, and the other substituents have the meanings as defined in formula I above.

The reaction is preferably carried out in the presence of a hydrogen halide acceptor, suitably a tertiary amine such as triethylamine and optionally in an organic solvent, for example, a hydrocarbon such as benzene or toluene.

The cyclopropane derivatives of the invention are of interest as pesticides particularly as insecticides and acaricides for agricultural and domestic outlets. The invention includes therefore within its scope pesticidal compositions comprising a carrier and/or a surface-active agent together with, as active ingredient, a cyclopropane derivative of formula I. Likewise the invention also includes a method of combating insect and/or arachnid pests at a locus which comprises applying to the locus a pesticidally effective amount of a cyclopropane derivative or composition of the invention.

The term 'carrier' as used herein means a solid or fluid material, which may be inorganic or organic and of synthetic or natural origin, with which the active compound is mixed or formulated to facilitate its application to the plant, seed, soil or other object to be treated, or its storage, transport or handling. The carrier may be a solid or a fluid. Any of the materials usually applied in formulating pesticides may be used as the carrier.

Suitable solid carriers are natural and synthetic clays and silicates, for example, natural silicas such as diatomacious earths; magnesium silicates, for example, talcs; magnesium aluminum silicates, for example, attapulgites and vermiculites; aluminum silicates, for example, kaolinites, montmorillinites and micas; calcium carbonates; calcium sulphate; synthetic hydraged silicon oxides and synthetic calcium or aluminum silicates; elements such as for example, carbon and sulphur; natural and synthetic resins such as, for example, coumarone resins, polyvinyl chloride and styrene polymers and copolymers; solid polychlorophenols; bitumen; waxes such as for example, beeswax, paraffin wax, and chlorinated mineral waxes; and solid fertilizers, for example, superphosphates.

Examples of suitable fluid carriers are water, alcohols, such as for example, isopropanol, glycols, ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosine, light mineral oils; chlorinated hydrocarbons, such as for example, carbon tetrachloride, perchloroethylene, trichloroethane, including liquefied normally vaporous gaseous compounds. Mixtures of different liquids are often suitable.

The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols for example p-octylphenol or p-octycresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example, sodium lauryl sulphate, sodium secondary alkyl sulphates, sodium salts of sulphonated castor oil, and sodium alkylaryl sulphonates such as sodium dodecylbenzene sulphonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates and aerosols and will generally contain 0.5 to 95% w, preferably 0.5 to 75% w, of toxicant. Wettable powders are usually compounded to contain 25, 50 or 75% w of toxicant and usually contain, in addition to solid carrier, 3–10% w of a dispersing agent and, where necessary, 0–10% w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of toxicant. Granules are usually prepared to have a size between 10 and 100 BS mesh (1.676 – 0.152 mm), and may be manufactured by agglomeration or impregnation techniques. Generally, granules will contain ½–25% w toxicant and 0–10% w of additives such as stabilizers, slow release modifiers and binding agents. Emulsifiable concentrates usually contain, in addition to the solvent and, when necessary, co-solvent, 10–50% w/v toxicant, 2–20% w/v emulsifiers and 0–20% w/v of appropriate additives such as stabilizers, penetrants and corrosion inhibitors. Suspension concentrates are compounded so as to obtain a stable, non-sedimenting, flowable product and usually contain 10–75% w toxicant, 0.5–15% w of dispersing agents, 0.1–10% w of suspending agents such as protective colloids and thixotropic agents, 0–10% w of appropriate additives such as defoamers, corrosion inhibitors, stabilizers, penetrants and stickers, and as carrier, water or an organic liquid in which the toxicant is substantially insoluble; certain organic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick 'mayonnaise'-like consistency.

The compositions of the invention may also contain other ingredients, for example, other compounds possessing pesticidal, for example, insecticidal, acaricidal, herbicidal or fungicidal properties.

The invention is illustrated further in the following examples:

EXAMPLE 1

Alpha-Ethynyl-3-phenoxybenzyl 2,2-dichloro-3,3-dimethyl-cyclopropane carboxylate 2,2-dichloro-3,3-dimethylcyclopropanoyl chloride (2.7g), alpha-ethynyl-3-phenoxybenzyl alcohol (3.0g) and triethylamine (3.0g) were dissolved in toluene (65 ml) at 10° C and the solution was stirred at room temperature for 16 hours. The mixture was filtered and the solvent was removed from the filtrate under reduced pressure. The residue was purified by chromatography on silica gel using toluene as eluant to give the desired product as an oil $n_D^{20}$ 1.5660.

Analysis. Calculated for $C_{21}H_{18}O_3Cl_2$: C64.9; H 4.6; Cl 18.2%. Found: C64.7; H 4.7; Cl 18.2%

EXAMPLE 2

Following a procedure similar to that of Example 1, further compounds were prepared whose physical characteristics and analyses are set out in Table 1.

TABLE I

| Compound | Refractive Index | Analysis | | |
|---|---|---|---|---|
| 1-(3-phenoxyphenyl)ethyl 2,2-dichloro-3,3-dimethyl-cyclopropane-carboxylate | $n_D^{20}$ 1.5560 | Calculated for $C_{20}H_{20}O_3Cl_2$<br>Found | : | C 63.3; H 5.3; Cl 18.7%<br>C 63.0; H 5.4; Cl 18.7% |
| α-allyl-3-phenoxybenzyl 2,2-dichloro-3,3-dimethyl-cyclopropane-carboxylate | $n_D^{20}$ 1.5530 | Calculated for $C_{22}H_{22}O_3Cl_2$<br>Found | : | C 65.2; H 5.5; Cl 17.5%<br>C 65.6; H 5.6; Cl 17.6% |
| α-phenyl-3-phenoxybenzyl 2,2-dichloro 3,3-dimethyl-cyclopropane-carboxylate | $n_D^{20}$ 1.5690 | Calculated for $C_{25}H_{22}O_3Cl_2$<br>Found | : | C 68.0; H 5.0; Cl 16.1%<br>C 67.8; H 5.4; Cl 15.4% |
| 1-(3-phenoxyphenyl)allyl 2,2-dichloro-3,3-dimethylcyclopropane-carboxylate | $n_D^{20}$ 1.5620 | Calculated for $C_{21}H_{20}Cl_2O_3$<br>Found | : | C 64.5; H 5.1%<br>C 64.8; H 5.3% |
| 1-(3-phenoxyphenyl)-3-phenyl-prop-2-ynyl-2,2-dichloro-3,3-dimethyl-cyclopropane-carboxylate | $n_D^{20}$ 1.5980 | Calculated for $C_{27}H_{22}Cl_2O_3$<br>Found | : | C 69.7; H 4.8%<br>C 69.7; H 4.8% |
| α-cyanomethyl-3-phenoxybenzyl 2,2-dichloro-3,3-dimethylcyclopropane-carboxylate | $n_D^{20}$ 1.5578 | Calculated for $C_{21}H_{18}Cl_2NO_3$<br>Found | : | C 62.4; H 4.7; N 3.5%<br>C 62.3; H 5.0 N 3.1% |
| 1-(3-(2-propynyloxy)phenyl)ethyl 2,2-dichloro-3,3-dimethylcyclopropane-carboxylate | $N_D^{20}$ 1.5351 | Calculated for $C_{17}H_{18}Cl_2O_3$<br>Found | : | C 59.8; H 5.3%<br>C 60.1; H 5.2% |

EXAMPLE 3

Insecticidal and Acaricidal Activity

The insecticidal and acaricidal activity of the compounds of the invention was tested as follows:

I. A 1.0% by weight solution in acetone of the compound to be tested was prepared and taken up in a micrometer syringe. Two to three-day old adult female house flies (*Musca domestica*) were anaesthetized with carbon dioxide, and 1 μl drop of the test solution was brushed off on the ventral abdomen of each, 20 flies being treated. The treated flies were held for 24 hours in glass jars, each containing a little granulated sugar as food for the flies, and the percentage of dead and moribund individuals was then recorded.

II. The compounds were formulated as solutions or suspensions containing 20% by weight of acetone and 0.05% by weight of Triton X 100 as wetting agent. The formulations contained 0.7% by weight of the compound to be tested. Turnip and broad bean plants, trimmed to one leaf each, were sprayed on the under surface of the leaf with the above formulations. Spraying was effected with a spraying machine delivering 450 liters per hectare, the plants passing under the spray on a moving belt. Ten adult 1–2 week-old mustard beetles (*Phaedon cochleariae*) were placed on the sprayed leaf of each turnip plant and ten apterous (6-day-old) vetch aphids (*Megoura viciae*) were placed on the sprayed leaf of each broad bean plant. The plants were then enclosed in glass cylinders fitted at one end with a muslin cap. Mortality counts were made after 24 hours.

III. In tests against glass house spider mites (*Tetranychus urticae*), leaf discs cut from French bean plants were sprayed in the manner described under II. One hour after spraying, the discs were inoculated with 10 adult mites. Mortality counts were made 24 hours after inoculation.

IV. In tests against large white butterfly larvae (*Pieris brassicae*), leaf discs cut from cabbage leaves were sprayed in the manner described under II. 10 3rd instar (8–10 day-old) larvae were placed on the discs within petri-dish pairs. Mortality counts were again 24 hours after inoculation.

The results of these tests are shown in Table 2, in which A denotes complete kill, B some kill and C no kill of the test species, and the test species are designated as follows:

M.d. = *Musca domestica*
P.c. = *Phaedon cochleariae*
P.b. = *Pieris brassicae*
M.v. = *Megoura viciae*
T.u. = *Tetranychus urticae*

TABLE 2

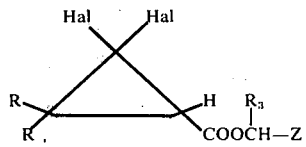

| Compound | | Pesticidal Activity | | | | |
|---|---|---|---|---|---|---|
| $R_3$ | Z | M.d | P.c | P.b | M.v | T.u |
| $CH_3$ | 3-phenoxyphenyl | A | B | A | B | A |
| $CH_2CH=CH_2$ | 3-phenoxyphenyl | A | B | A | A | A |
| $C_6H_5$ | 3-phenoxyphenyl | B | B | A | B | C |
| $C\equiv CH$ | 3-phenoxyphenyl | A | A | A | A | A |
| $CH=CH_2$ | 3-phenoxyphenyl | A | B | — | A | B |
| $C\equiv C-C_6H_5$ | 3-phenoxyphenyl | A | C | — | A | B |
| $CH_3$ | 3-propynyloxyphenyl | A | C | A | A | A |

We claim:
1. A method of combating insect or arachnid pests at a locus which comprises applying to the locus a pesticidally effective amount of a cyclopropane derivative of the formula

$$\begin{array}{c} \text{Hal} \quad \text{Hal} \\ R \diagup\!\!\!\diagdown H \quad R_3 \\ R \quad \text{COOCH-Z} \end{array}$$

wherein R represents alkyl of 1 to 6 carbon atoms; each Hal represents a halogen atom; $R_3$ represents alkyl, cycloalkyl, cyanoalkyl ar alkenyl of up to 6 carbon atoms, alkynyl of up to 8 carbon atoms or a phenyl group; and Z represents phenoxyphenyl or propynyloxyphenyl.

2. A method as claimed in claim 1 wherein each Hal represents a chlorine atom; $R_3$ represents an alkyl, cycloalkyl, cyanoalkyl, or alkenyl group of up to 6 carbon atoms, alkynyl of up to 8 carbon atoms, or phenyl.

3. A method as claimed in claim 2, wherein each R represents a methyl group and $R_3$ represents a methyl, cyanomethyl, propenyl, vinyl, ethynyl, phenylethynyl, cyclohexyl or phenyl group.

4. A method as claimed in claim 3, wherein $R_3$ is methyl.

5. A method as claimed in claim 3 wherein Z represents a phenoxyphenyl group.

6. A method as claimed in claim 5 wherein $R_3$ is allyl.

7. A method as claimed in claim 5 wherein each R represents a methyl group; and $R_3$ represents a methyl, propenyl, ethynyl or phenyl group.

8. A method as claimed in claim 7, wherein $R_3$ is ethynyl.

9. A method as claimed in claim 7, wherein $R_3$ is phenyl.

10. An insecticidal composition comprising at least one carrier or surface active agent together with, as active ingredient, an insecticidally effective amount of a cyclopropane derivative as claimed in claim 7.

UNITED STATES PATENT AND TRADEMARK OFFICE
CERTIFICATE OF CORRECTION

PATENT NO. : 3,993,774
DATED : November 23, 1976
INVENTOR(S) : ROBERT J. G. SEARLE and ROGER E. WOODALL It is certified that error appears in the above-identified patent and that said Letters Patent are hereby corrected as shown below:

Claim 1, column 6, line 33, change "ar" to

-- or --.

Claim 10, column 6, line 59 change "7" to

-- 1 --.

Signed and Sealed this

Fifteenth Day of February 1977

[SEAL]

Attest:

RUTH C. MASON
*Attesting Officer*

C. MARSHALL DANN
*Commissioner of Patents and Trademarks*